United States Patent
Saito et al.

(10) Patent No.: US 9,266,916 B2
(45) Date of Patent: Feb. 23, 2016

(54) PRODUCTION METHOD FOR DODECACARBONYL TRIRUTHENIUM

(71) Applicant: Tanaka Kikinzoku Kogyo K.K., Tokyo (JP)

(72) Inventors: Masayuki Saito, Tsukuba (JP); Hirofumi Nakagawa, Tsukuba (JP); Toshiyuki Shigetomi, Tsukuba (JP); Kenji Goto, Tsukuba (JP)

(73) Assignee: Tanaka Kikinzoku Kogyo K.K., Chiyoda-ku, Tokyo (JP)

( * ) Notice: Subject to any disclaimer, the term of this patent is extended or adjusted under 35 U.S.C. 154(b) by 0 days.

(21) Appl. No.: 14/655,076

(22) PCT Filed: Jan. 20, 2014

(86) PCT No.: PCT/JP2014/050907
§ 371 (c)(1),
(2) Date: Jun. 24, 2015

(87) PCT Pub. No.: WO2014/112613
PCT Pub. Date: Jul. 24, 2014

(65) Prior Publication Data
US 2015/0344510 A1    Dec. 3, 2015

(30) Foreign Application Priority Data
Jan. 21, 2013    (JP) ................. 2013-007977

(51) Int. Cl.
*C07F 15/00*    (2006.01)
(52) U.S. Cl.
CPC ................. *C07F 15/0046* (2013.01)
(58) Field of Classification Search
CPC .................................................. C07F 15/0046
USPC .......................................... 556/136; 427/252
See application file for complete search history.

(56) References Cited

U.S. PATENT DOCUMENTS 3,561,924 A * 2/1971 Candlin ............... C01G 55/007
                                                                     423/418
3,786,132 A    1/1974 Dawes et al.

FOREIGN PATENT DOCUMENTS

| GB | 1047794 | * 11/1966 |
| GB | 1060938 A | 3/1967 |
| GB | 1160765 A | 8/1969 |
| JP | 1-188429 | 7/1989 |
| JP | 7-316175 | 12/1995 |

OTHER PUBLICATIONS

Elena Lucenti et al., "Reproducible high-yield syntheses of $[Ru_3(CO)_{12}]$, $[H_4Ru_4(CO)_{12}]$, and $[Ru_6C(CO)_{16}]^{2-}$ by a convenient two-step methodology involving controlled reduction in ethylene glycol of $RuCl_3$—$nH_2O$", Journal of Organometallic Chemistry 669 (2003) 44-47, www.elsevier.com/locate/organchem.
Matthieu Fauréet al., 24. Dodecacarbonyltriruthenium, $Ru_3(CO)_{12}$, Inorganic Syntheses, vol. 34, Chapter Three, Transition Metal Carbonyl Compounds, 2004, John Wiley & Sons, Inc.
International Search Report PCT/JP2014/050907, Apr. 8, 2014.

* cited by examiner

*Primary Examiner* — Porfirio Nazario Gonzalez
(74) *Attorney, Agent, or Firm* — Orrick Herrington & Sutcliffe, LLP

(57) ABSTRACT

The present invention is a method for producing dodecacarbonyl triruthenium (DCR) including a process of carbonylating ruthenium chloride with carbon monoxide, in which an amine is added to a reaction system at 0.8 molar equivalent or more with respect to chlorine of the ruthenium chloride and the carbonylation is conducted at a reaction temperature of 50 to 100° C. and a reaction pressure of 0.2 to 0.9 MPa. According to the present invention, it is possible to produce dodecacarbonyl triruthenium having less residual impurity metals without applying a reaction condition of a high pressure.

8 Claims, 1 Drawing Sheet

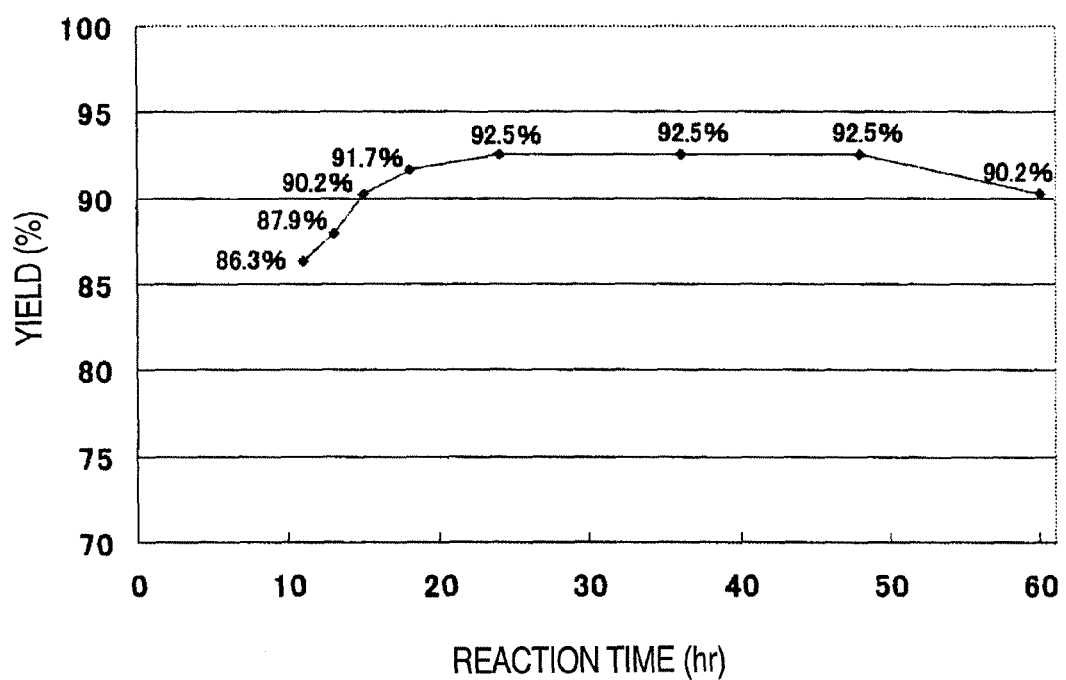

PRODUCTION METHOD FOR DODECACARBONYL TRIRUTHENIUM

TECHNICAL FIELD

The present invention relates to a method for producing dodecacarbonyl triruthenium which is useful as a raw material for producing a ruthenium thin film or a ruthenium compound thin film by a chemical deposition method.

BACKGROUND ART

Hitherto, a number of organic ruthenium compounds have been known as a starting compound when producing a ruthenium thin film or a ruthenium compound thin film by a chemical deposition method such as a CVD method (chemical vapor deposition method) and an ALD method (atomic layer deposition method). There is dodecacarbonyl triruthenium (hereinafter, referred to as DCR) represented by the following Formula as the compound under investigation for practical use in recent years among the organic ruthenium compounds.

[Chemical Formula 1]

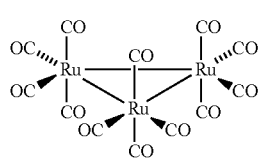

DCR is a substance which is solid (orange crystal) at room temperature and has a melting point of 154 to 155° C. The utilization of DCR is expected from the reasons that DCR has a simple molecular structure including Ru and CO and can be deposited by only the thermal decomposition without the use of a reactant gas and thus there is an advantage that impurities such as hydrocarbons hardly remain in the deposited thin film and the production efficiency of thin film is not adversely affected by the specification adjustment of the raw material container or the appropriate process control even if it is a solid raw material.

As the method for producing DCR, a method is basic in which a ruthenium compound as the raw material is carbonylated with carbon monoxide. In addition, ruthenium chloride is often applied as the ruthenium compound of the raw material. Ruthenium chloride is the most inexpensive and easily available among various kinds of ruthenium compounds and widely used as a raw material for a number of ruthenium complexes other than DCR.

Moreover, as the method for producing DCR to use ruthenium chloride as the raw material, the simplest method is a method in which ruthenium chloride reacts in a carbon monoxide atmosphere at a high pressure (several tens to 100 MPa) (see Patent Document 1). In addition, a method is also known in which a metal such as zinc metal or a metal salt such as KOH and Na2CO3 are added into the reaction system for the purpose of lowering the reaction pressure and ruthenium chloride is carbonylated (see Patent Document 2 and Non Patent Documents 1 and 2).

Furthermore, a method is also known in which an intermediate is produced using ruthenium chloride as the starting material and this is then carbonylated. There is a method in which, for example, ruthenium acetylacetonate obtained by reacting ruthenium chloride with an acetylacetonato salt is produced as an intermediate and this intermediate is carbonylated (see Patent Document 3).

RELATED ART DOCUMENT

Patent Documents

Patent Document 1: U.S. Pat. No. 3,786,132
Patent Document 2: GB 1,160,765
Patent Document 3: GB 1,060,938

Non Patent Documents

Non Patent Document 1: Elena Lucenti et al., "Reproducible high-yield syntheses of [Ru3(CO)12], [H4Ru(CO)12], and [Ru6C(CO)16]2-by a convenient two-step methodology involving controlled reduction in ethylene glycol of RuCl3.nH2O", J. Oranometalic. chem, 669 (2003), p 44-47
Non Patent Document 2: MATTHIEU FAURE et al., "DODECACARBONYL TRI RUTHENIUM, $Ru_3(CO)_{12}$", Inorganic Synthesis, 34 (2004), p 110-115

SUMMARY OF THE INVENTION

Problems to be Solved by the Invention

In the conventional methods for producing DCR, there are the following problems. That is, in the method to react carbon monoxide having a high pressure, the producing apparatus needs to be equipped with a high pressure specification and to secure safety, and thus the cost for facility increases, which is reflected to the production cost of DCR.

In addition, there is a concern that the metal remains in produced DCR in the case of adding a metal salt or the like. This impurity metal can be removed to some extent by setting the purification process but an increase in number of processes leads to higher production costs. In addition, the impurity metal cannot always be completely removed even though the purification process is set. Forming a thin film using DCR which contains an impurity metal even in a small amount may be a cause for the metal to remain also in the thin film.

Furthermore, also in the case of producing DCR via an intermediate, an increase in number of processes for the production of intermediate leads to higher production costs. In addition, in the case of the method via an intermediate, the yield obtained when converting the starting material to the intermediate affects the yield of DCR and thus the final yield of DCR often decreases.

The present invention has been made based on the above-mentioned problems, and provided is a method for producing DCR in which ruthenium chloride is directly carbonylated without being converted to an intermediate, the impurity metal does not remain, and a high pressure condition is not required.

Means for Solving the Problems

The present inventors have conducted intensive investigations to solve the above problems and have found out that the reaction in the carbonylation process of ruthenium chloride proceeds even under a low pressure of carbon monoxide by adding an amine to the reaction system as a substance having a catalytic function. An amine does not contain a metal as apparent from its chemical formula and becomes a chloride in the carbonylation reaction of ruthenium chloride and thus can be separated from the reaction product (DCR). Hence, there is no concern that a metal remains in produced DCR. Moreover, the results of the investigations by the present inventors reveal that the addition of an amine makes it possible for the synthesis reaction of DCR to proceed although the reaction pressure is greatly lowered than in the conventional art.

However, it may be said that it is insufficient for practical use that the reaction simply proceeds although an amine has a catalytic function on the carbonylation reaction of ruthenium chloride. Hence, the present inventors have conducted further investigations on the ranges of condition factors which affect the yield of DCR in the carbonylation reaction of ruthenium chloride in the presence of an amine. As a result, it has been found out that it is possible to produce DCR with a favorable yield by strictly setting the reaction temperature in addition to the reaction pressure.

That is, the present invention is a method for producing dodecacarbonyl triruthenium represented by the following Formula, the method including a process of carbonylating ruthenium chloride with carbon monoxide, wherein an amine is added to the reaction system at 0.8 molar equivalent or more with respect to chlorine of the ruthenium chloride and the carbonylation is conducted at a reaction temperature of 50 to 100° C. and a reaction pressure of 0.2 to 0.9 MPa.

Hereinafter, the method for producing DCR according to the present invention will be described in detail. Ruthenium chloride of the raw material is preferably those which are in a solution state. The solvent in the case is preferably an alcohol of an organic solvent in which ruthenium chloride is highly soluble but DCR of the product hardly dissolves. Methanol, ethanol, propanol (1-propanol and isopropyl alcohol) and butanol (1-butanol and isobutanol) are preferable from the viewpoint of being easily dried after the synthesis of DCR in particular. In addition, it is preferable that the solvent has a low water content and is in a closely dry state. This is because there is a tendency that the yield of DCR greatly decreases when a solvent having a high water content is used. Specifically, the water content in the solvent is preferably 0 to 5% by mass, more preferably 0 to 3% by mass and even the most preferably 0 to 1% by mass. Furthermore, the concentration of ruthenium chloride in the ruthenium chloride solution is preferably 25 to 150 g/L since the reaction efficiency falls when the concentration is low and by-products are likely to be produced when the concentration is too high. Incidentally, it is preferable to remove solid matters by appropriately conducting the filtration when preparing the ruthenium chloride solution.

The ruthenium chloride solution prepared is introduced into a reaction vessel. The reaction vessel is preferably a closed type and its constituent material is preferably a metal (stainless steel or the like) excellent in corrosion resistance. Thereafter, an amine is added to the ruthenium chloride solution. Amines are a compound in which at least one functional group such as a hydrocarbon group bonds with nitrogen, but it has been discussed by the present inventors that the catalytic function of an amine on the synthesis reaction of DCR is exhibited by the presence of at least one nitrogen-carbon bond. Hence, in the present invention, any of a primary amine, a secondary amine and a tertiary amine which have 1 to 3 nitrogen-carbon bonds can be applied.

The amine applied in the present invention is preferably an amine having 3 to 36 carbon atoms. The functional group bonded to nitrogen may contain oxygen in addition to those including carbon and hydrogen, and an amine in which an alkyl group, an alcohol, a benzene ring and the like are bonded to nitrogen can be applied. Specific examples of amines may include propylamine, diethylamine, triethylamine, ethanolamine, diethanolamine, triethanolamine, tris[2-(2-methoxyethoxy)ethyl]amine and N,N-dimethylaniline.

The amount of amine added is 0.8 molar equivalent or more with respect to the amount of chlorine in ruthenium chloride. The synthesis reaction of DCR does not proceed when an amine is added at less than 0.8 molar equivalent, and thus the yield is significantly low. Incidentally, the upper limit is preferably 2.0 molar equivalents since the yield does not increase although an amine is excessively added but the cost for chemicals increases. Incidentally, chlorine herein refers to a chlorine atom.

Thereafter, carbon monoxide gas is introduced into the ruthenium chloride solution, the reaction pressure and the reaction temperature are set to the above ranges, and DCR is synthesized. The reaction pressure is set to 0.2 to 0.9 MPa because the synthesis reaction hardly proceeds at less than 0.2 MPa and thus the yield of DCR deteriorates. On the other hand, this is because there is a possibility that residues are formed in the reaction solution in the case of more than 0.9 MPa and the residues affect the quality and yield of DCR.

The reaction temperature is set to 50 to 100° C. because the yield of DCR sharply decreases in the case of higher than 100° C. The upper limit of this reaction temperature is preferably 90° C. On the other hand, such a sharp decrease in yield is not observed in a case in which the reaction temperature is low, but the yield gradually decreases along with a decrease in reaction temperature, and thus the lower limit value is set to 50° C. from a practical point of view. Incidentally, the relation between the reaction temperature and the yield slightly differs depending on the reaction scale (quantity of production of DCR), and particularly the value of the above-mentioned reaction temperature at which the yield sharply decreases slightly differs depending on the reaction scale. The temperature range of 50 to 100° C. regulated by the present invention indicates the range in which a practical yield can be obtained even when the reaction scale changes. Upon implementing the present invention, it is possible to set an optimum reaction temperature in accordance with the reaction scale within the above range.

As described above, in the present invention, a strict adjustment of the reaction pressure and reaction temperature is required together with the addition of an amine to the reaction system. This is because the yield of DCR is particularly highly sensitive to the two factors of the reaction pressure and the reaction temperature.

The reaction time for the synthesis reaction of DCR is preferably 10 to 30 hours. There is a tendency that the yield increases as the reaction time is longer, and the yield is insufficient when the reaction time is shorter than 10 hours. However, an increase in yield is not observed but there is rather a possibility of a decrease in yield even when the reaction time is longer than 30 hours, and thus it is preferable to set the upper limit to 30 hours. Incidentally, it is preferable to stir the solution during this synthesis reaction.

Solid DCR is precipitated by the above synthesis reaction of DCR. It is possible to collect DCR by filtering off the solution after the reaction and appropriately performing drying.

DCR obtained by the above processes may be subjected to the purification if necessary. This purification process is preferably conducted by a sublimation method. The purification by the sublimation method is more suitable than the purification by recrystallization, column chromatography and the like since DCR is solid, has a high melting point, and also is poorly soluble in the solvent. The conditions for purification by the sublimation method are as follows. The degree of vacuum is 50 Pa or less, the heating temperature is 80 to 110° C. and the cooling temperature is 20° C. or lower. The sublimation rate decreases when the degree of vacuum is more than 50 Pa, and thus the sublimation time is greatly prolonged. The sublimation time is greatly prolonged when the heating temperature is lower than 80° C., and there is a concern that the thermal decomposition of DCR partially occurs although the sublimation rate is faster when the heating temperature is higher than 110° C. and consequently the yield greatly decreases. Incidentally, other purification methods (recrystallization, column chromatography and the like) may be used although the sublimation method is suitable for the purification process.

Advantageous Effects of the Invention

As described above, the method for producing DCR of the present invention is a method to conduct the synthesis reaction of DCR using an amine as a substance that hardly becomes a cause of an impurity as the catalytic additive. In the present invention, it is possible to synthesize DCR without setting the reaction pressure to a high pressure. Moreover, a suitable yield of DCR is achieved by strictly setting the reaction temperature and the reaction pressure. According to the method for producing DCR of the present invention, it is possible to produce high-quality DCR containing no impurities at a low cost.

BRIEF DESCRIPTION OF THE DRAWINGS

FIG. 1 is a diagram illustrating the relation between the reaction time and the yield of DCR in a second embodiment.

DESCRIPTION OF EMBODIMENTS

First Embodiment

In this embodiment, a synthesis test to confirm the presence or absence of the effect by the addition of an amine to the reaction system for DCR synthesis was performed. The production process of DCR is as follows. Ruthenium chloride (manufactured by Tanaka Kikinzoku Kogyo K. K., ruthenium chloride content: 38.67 wt %, chlorine content: 47.4 wt %) and 1-propanol were mixed and stirred to prepare a ruthenium chloride solution, and this was introduced into an autoclave (made of steel) having a capacity of 100 ml of the reaction vessel. Thereafter, an amine was added into the reaction vessel and further carbon monoxide was air tightly introduced into the reaction vessel until to have a predetermined reaction pressure. Thereafter, the temperature was raised to the reaction temperature while maintaining the predetermined reaction pressure with carbon monoxide, and the synthesis reaction of DCR was allowed to proceed. The solution was stirred during the reaction. The reaction conditions in the present embodiment were as follows. In the present embodiment, DCR was synthesized using a plurality of amines which has different numbers of carbon atoms. In addition, the possibility of the synthesis of DCR in the case of not adding an amine was also investigated.

Ruthenium chloride: 1.58 g (Ru: 0.61 g)
1-propanol: 60 mL
Amine: added by 1.3 molar equivalents with respect to chlorine for each amine
Propylamine (1.57 g)
Diethylamine (1.94 g)
Triethylamine (2.69 g)
Trioctylamine (9.40 g)
Tridodecylamine (13.87 g)
Triethanolamine (3.97 g)
Tris[2-(2-methoxyethoxyl)ethyl]amine (8.60 g)
N,N-dimethylaniline (3.22 g)
Not added
Reaction pressure: 0.35 MPa
Reaction temperature: 85° C.
Reaction time: 15 hours
Stirring speed: 300 rpm After completion of the reaction, precipitated crystals were filtered and vacuum-dried for collection of the orange crude crystals of DCR, and the yield was calculated. The reaction test was performed for the presence or absence of amine addition. The results of this reaction test are presented in Table 1.

TABLE 1

| | Amine | Yield |
|---|---|---|
| Example 1 | Propylamine | 56.4% |
| Example 2 | Diethylamine | 74.6% |
| Example 3 | Triethylamine | 90.2% |
| Example 4 | Trioctylamine | 89.5% |
| Example 5 | Tridodecylamine | 62.8% |
| Example 6 | Triethanolamine | 60.1% |
| Example 7 | Tris[2-(2-methoxyethoxy)ethyl]amine | 55.2% |
| Example 8 | N,N-dimethylaniline | 50.3% |
| Comparative Example 1 | Not added | 0% |

The precipitate was not observed at all in the solution after the reaction in a case in which no amine was added to the reaction system (Comparative Example 1). On the other hand, DCR was successfully obtained with a high yield of 90.2% in Example 3 in which an amine was added. From this result, it can be said that an amine is essential for the synthesis of DCR in a low pressure.

In addition, with regard to the amines added, it is possible to obtain DCR regardless of the numbers of functional groups (primary to tertiary). In addition, with regard to the kinds of functional groups, an amine which has a hydrocarbon group containing oxygen, such as an alcohol can also contribute to the synthesis reaction of DCR other than a hydrocarbon group including carbon and hydrogen, such as an alkyl group.

Second Embodiment

In this embodiment, the suitable ranges of various kinds of reaction conditions were investigated. That is, the ranges of the amount of amine (the equivalent number with respect to chlorine) added, the reaction pressure, the reaction temperature, the reaction time and the water content of solvent in order to obtain a suitable yield of DCR were investigated while changing the respective conditions. Incidentally, triethylamine was used as the amine in the present embodiment.

[Amount of Amine Added]

The reaction test of DCR was performed with the additive amount of triethylamine changed. The basic processes were the same as those in the first embodiment. The reaction conditions were as follows. In this test, the measurement results of the yield of DCR with respect to the additive amount of triethylamine are shown in Table 2.

Ruthenium chloride: 1.58 g (Ru: 0.61 g)
1-propanol: 60 mL
Triethylamine: 0.5 equivalent, 0.6 equivalent, 0.8 equivalent, 1.0 equivalent, 1.3 equivalents, 1.5 equivalents and 1.8 equivalents (molar equivalent with respect to chlorine)

Reaction pressure: 0.35 MPa
Reaction temperature: 85° C.
Reaction time: 15 hours
Stirring speed: 300 rpm

TABLE 2

|  | Additive amount of amine | Yield |
| --- | --- | --- |
| Comparative Example 2 | 0.5 molar equivalent | 0% |
| Comparative Example 3 | 0.6 molar equivalent | 0% |
| Example 9 | 0.8 molar equivalent | 56.2% |
| Example 10 | 1.0 molar equivalent | 78.5% |
| Example 11 | 1.3 molar equivalents | 90.2% |
| Example 12 | 1.5 molar equivalents | 84.0% |
| Example 13 | 1.8 molar equivalents | 81.6% |

As can be seen from Table 2, DCR is not synthesized when the additive amount of amine (molar equivalent number with respect to chlorine) is 0.5 molar equivalent and 0.6 molar equivalent. Hence, it is required to add an amine at 0.8 molar equivalent or more.

[Reaction Pressure]

With regard to the pressure of carbon monoxide in the synthesis reaction, the reaction test of DCR was performed with the pressure value changed. The basic processes were the same as those in the first embodiment. The reaction conditions were as follows. The measurement results of the yield of DCR in this test are shown in Table 3.

Ruthenium chloride: 1.58 g (Ru: 0.61 g)
1-propanol: 60 mL
Triethylamine: 1.3 equivalents (molar equivalent with respect to chlorine)
Reaction pressure: 0.1 MPa, 0.2 MPa, 0.3 MPa, 0.35 MPa, 0.5 MPa, 0.78 MPa, 0.9 Mpa and 1.0 MPa
Reaction temperature: 85° C.
Reaction time: 6 hours
Stirring speed: 300 rpm

TABLE 3

|  | Reaction pressure | Yield |
| --- | --- | --- |
| Comparative Example 4 | 0.1 MPa | 0% |
| Example 14 | 0.2 MPa | 62.5% |
| Example 15 | 0.3 MPa | 90.1% |
| Example 16 | 0.35 MPa | 91.7% |
| Example 17 | 0.5 MPa | 89.4% |
| Example 18 | 0.78 MPa | 78.5% |
| Example 19 | 0.9 MPa | 70.2% |
| Comparative Example 5 | 1.0 MPa | 65.0% |

As can be seen from Table 3, it is possible to allow the synthesis reaction of DCR to proceed at a reaction pressure of 0.2 MPa or more. However, the yield was slightly inferior and the contamination of DCR obtained with a black residue was observed at the reaction pressure of 1.0 MPa. Hence, a high reaction pressure is considered to be not preferable from the viewpoint of quality. It has been confirmed that it is required to set the reaction pressure to a range of 0.2 to 0.9 MPa from these results.

[Reaction Temperature]

With regard to the reaction temperature, the reaction test of DCR was performed with the temperature value changed. The basic processes were the same as those in the first embodiment. The reaction conditions were as follows. The measurement results of the yield of DCR in this test are shown in Table 4.

Ruthenium chloride: 1.58 g (Ru: 0.61 g)
1-propanol: 60 mL
Triethylamine: 1.3 equivalents (molar equivalent with respect to chlorine)
Reaction pressure: 0.35 MPa
Reaction temperature: 40° C., 50° C., 75° C., 80° C., 85° C., 90° C., 100° C. and 110° C.
Reaction time: 15 hours
Stirring speed: 300 rpm

TABLE 4

|  | Reaction temperature | Yield |
| --- | --- | --- |
| Comparative Example 6 | 40° C. | 12.5% |
| Example 20 | 50° C. | 55.3% |
| Example 21 | 75° C. | 84.0% |
| Example 22 | 80° C. | 86.3% |
| Example 23 | 85° C. | 90.2% |
| Example 24 | 90° C. | 81.6% |
| Example 25 | 100° C. | 77.7% |
| Comparative Example 7 | 110° C. | 34.7% |

For the synthesis reaction of DCR of the present invention, it has been confirmed that it is not always preferable that the reaction temperature is higher, and a great decrease in yield has been observed at 110° C. In this regard, the yield at 100° C. (77.7%) is not a low value but it is reasonable to set the upper limit to 100° C. when a decrease in yield by the change of the reaction scale is assumed.

[Reaction Time]

The reaction test of DCR was performed by changing the reaction time after the addition of triethylamine and carbon monoxide to the ruthenium chloride solution. The basic processes were the same as those in the first embodiment. The reaction conditions were as follows. The measurement results of the yield of DCR in this test are illustrated in FIG. 1.

Ruthenium chloride: 1.58 g (Ru: 0.61 g)
1-propanol: 60 mL
Triethylamine: 1.3 equivalents (molar equivalent with respect to chlorine)
Reaction pressure: 0.35 MPa
Reaction temperature: 85° C.
Reaction time: 11 to 60 hours
Stirring speed: 300 rpm As the effect of the reaction time on the yield of DCR, it can be said that a suitable yield is obtained when the reaction time is basically 10 hours or longer. The yield of DCR is in a steady state from the reaction time of 15 to 18 hours. A suitable yield is obtained even when the reaction time is longer, but it is preferable to set the reaction time to 10 to 30 hours since the production efficiency is affected by the length of reaction time.

[Water Content of Solvent]

The relation between the water content of 1-propanol before being used for the preparation of the ruthenium chloride solution and the yield of DCR was investigated. The production process of DCR other than this was the same as in the first embodiment. The reaction conditions were as follows. The measurement results of the yield of DCR in this test are shown in Table 5.

Ruthenium chloride: 1.58 g (Ru: 0.61 g)
1-propanol: 60 mL (water content: dry, 0.5 wt %, 1.0 wt %, 3.0 wt %, 5.0 wt %, 10 wt % and 30wt %)
Triethylamine: 1.3 equivalents (molar equivalent with respect to chlorine)
Reaction pressure: 0.35 MPa
Reaction temperature: 85° C.
Reaction time: 10 to 60 hours
Stirring speed: 300 rpm

TABLE 5

|  | Water content | Yield |
|---|---|---|
| Example 26 | 0% (dry) | 91.7% |
| Example 27 | 0.5% | 92.5% |
| Example 28 | 1% | 90.2% |
| Example 29 | 3% | 61.4% |
| Example 30 | 5% | 47.2% |
| Comparative Example 9 | 10% | 14.8% |
| Comparative Example 10 | 30% | 1.6% |

As can be seen from Table 5, there is a possibility that the yield of DCR is affected by the water content in the solvent. Moreover, it is not possible to obtain a practical yield of DCR in the case of using a solvent which contains water at 10% or more. From this fact, it is preferable to set the water content in the solvent to 5% by mass or less. However, it is not intended to require a dry state (water content of approximately 0%), and it is possible to obtain a high yield using a solvent having a water content of 1% or less.

[Analysis of Reaction Product]

With regard to DCR produced in each test described above, the component analysis was performed by the CHN elemental analysis method and the ruthenium content and carbon content in the product were measured. The results are shown in Table 6.

TABLE 6

|  | Ru (%) | C (%) |
|---|---|---|
| Product | 47.08 | 22.53 |
| Theoretical value | 47.43 | 22.54 |

As described above, it has been confirmed that DCR produced in the present embodiment have the constituents close to the theoretical value and can be used as a raw material for chemical deposition without any problem.

INDUSTRIAL APPLICABILITY

The method for producing DCR according to the present invention is a method in which the additive amount of amine and the reaction conditions are strictly set while adding an amine as a catalytic additive. Amines do not contain zinc, an alkali metal and the like, and thus the impurities are prevented from remaining in produced DCR. In addition, in the present invention, it is possible to synthesize DCR without setting the reaction pressure to a high pressure and to cut down the production cost. The method for producing DCR according to the present invention also provides a favorable yield.

The invention claimed is:

1. A method for producing dodecacarbonyl triruthenium having the following Formula, the method comprising a process of carbonylating ruthenium chloride with carbon monoxide,
wherein an amine is added to a reaction system at 0.8 molar equivalent or more with respect to chlorine of the ruthenium chloride and the carbonylation is conducted at a reaction temperature of 50 to 100° C. and a reaction pressure of 0.2 to 0.9 MPa

[Chemical Formula 1]

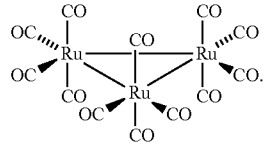

2. The method for producing dodecacarbonyl triruthenium according to claim 1, wherein an amine to be added is an amine having 3 to 36 carbon atoms.

3. The method for producing dodecacarbonyl triruthenium according to claim 1, wherein a reaction time is 10 to 30 hours.

4. The method for producing dodecacarbonyl triruthenium according to claim 1, wherein ruthenium chloride is a ruthenium chloride solution including ruthenium chloride and an organic solvent, and the organic solvent is methanol, ethanol, propanol and butanol.

5. The method for producing dodecacarbonyl triruthenium according to claim 4, wherein the organic solvent is an organic solvent having a water content of 5% by mass or less.

6. The method for producing dodecacarbonyl triruthenium according to claim 2, wherein a reaction time is 10 to 30 hours.

7. The method for producing dodecacarbonyl triruthenium according to claim 2, wherein ruthenium chloride is a ruthenium chloride solution including ruthenium chloride and an organic solvent, and the organic solvent is methanol, ethanol, propanol and butanol.

8. The method for producing dodecacarbonyl triruthenium according to claim 3, wherein ruthenium chloride is a ruthenium chloride solution including ruthenium chloride and an organic solvent, and the organic solvent is methanol, ethanol, propanol and butanol.

* * * * *